United States Patent [19]
Kleinman

[11] Patent Number: 5,147,873
[45] Date of Patent: Sep. 15, 1992

[54] AMINO-SUBSTITUTED BRIDGED AZABICYCLIC QUINOLONE CARBOXYLIC ACIDS AND ESTERS

[75] Inventor: Edward F. Kleinman, Pawcatuck, Conn.

[73] Assignee: Pfizer Inc., New York, N.Y.

[21] Appl. No.: 651,355

[22] Filed: Feb. 15, 1991

Related U.S. Application Data

[63] Continuation of PCT/US88/02908, Aug. 23, 1988.

[51] Int. Cl.$^5$ ............... A61K 31/535; A61K 31/47; C07D 401/10; C07D 498/06
[52] U.S. Cl. .................. 514/230.2; 514/294; 514/312; 544/101; 546/94; 546/156; 546/112; 546/183; 549/546; 564/373
[58] Field of Search ............... 544/101; 546/94, 156; 514/229.8, 294, 312, 230.2

[56] References Cited

U.S. PATENT DOCUMENTS

| | | | |
|---|---|---|---|
| 4,571,396 | 2/1986 | Hutt et al. | 514/249 |
| 4,775,668 | 10/1988 | Jefson et al. | 514/183 |
| 4,803,205 | 2/1989 | Bridges et al. | 514/254 |
| 4,920,120 | 4/1990 | Domagala et al. | 546/156 |

*Primary Examiner*—Mukund J. Shah
*Assistant Examiner*—E. Bernhardt
*Attorney, Agent, or Firm*—Peter C. Richardson; Paul H. Ginsburg; Gezina Holtrust

[57] ABSTRACT

Compounds of the formula

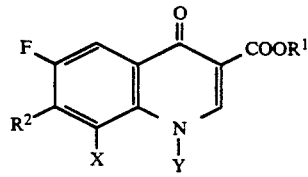

wherein $R^1$ is hydrogen, $C_1$–$C_6$ alkyl, or a pharmaceutically acceptable cation;
Y is cyclopropyl, ethyl or p-fluorophenyl, and X is hydrogen or fluoro, or X and Y taken together form a group

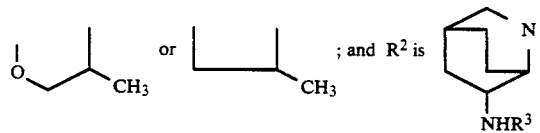

wherein $R^3$ is hydrogen or $C_1$–$C_4$ alkyl; or a pharmaceutically acceptable salt thereof. Also disclosed are antibacterial pharmaceutical compositions comprising the foregoing compounds, methods of using the compounds in treating bacterial infections, and intermediates for the preparation of the compounds.

21 Claims, No Drawings

AMINO-SUBSTITUTED BRIDGED AZABICYCLIC QUINOLONE CARBOXYLIC ACIDS AND ESTERS

This application is a continuation of PCT/US88/02908 filed on Aug. 23, 1988.

BACKGROUND OF THE INVENTION

This invention relates to substituted bridged-azabicycloalkyl quinolone carboxylic acids and esters, antibacterial compositions containing said compounds, methods of using said compounds, and intermediates for the preparation of said compounds.

European Patent Application 86307045.4 (Publication No. 0215650), and U.S. Pat. No. 4,571,396, refer to amino-substituted bridged azabicycloalkyl quinolone carboxylic acids and esters and antibacterial compositions containing those compounds. European Patent Application 83305148.5 (Publication No. 0106489) and International Application No. PCT/US87/01583 refer to bridged-diazabicycloalkyl quinolone carboxylic acids and esters and antibacterial compositions containing those compounds.

SUMMARY OF THE INVENTION

The present invention relates to compounds of the formula

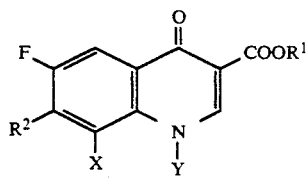

wherein $R^1$ is hydrogen, $C_1$–$C_6$ alkyl, or a pharmaceutically acceptable cation;

Y is cyclopropyl, ethyl or p-fluorophenyl, and X is hydrogen or fluoro, or X and Y taken together form a group

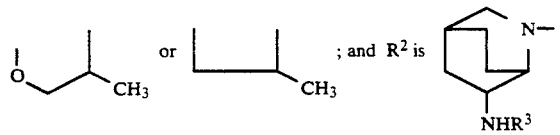

wherein $R^3$ is hydrogen or $C_1$–$C_4$ alkyl; or a pharmaceutically acceptable salt thereof.

The present invention also relates to pharmaceutical compositions comprising a pharmaceutically acceptable carrier or diluent and a compound of the formula I or a pharmaceutically acceptable salt thereof in an antibacterially effective amount.

The present invention also provides a method of treating an animal, including a human being, having a bacterial disease which comprises administering to the animal an antibacterially effective amount of a compound of the formula I or a pharmaceutically acceptable salt thereof.

The present invention also relates to methods of preparing the compounds of formula I and to intermediates for the preparation of the compounds of the formula I. Such intermediates include compounds of the formulae 2–17 described below.

The compounds of the present invention may have chiral centers in view of the bridged structures resulting in formation of steroisomers. These steroisomers may be designated with reference to R and S in accordance with standard nomenclature. The compounds of the invention include racemic mixtures and optical isomers.

Preferred compounds of the invention are those of formula I wherein $R^1$ is hydrogen or a pharmaceutically acceptable cation such as sodium or potassium.

Particularly preferred compounds are those wherein $R^1$ is hydrogen or a pharmaceutically acceptable cation Specific preferred compounds are:

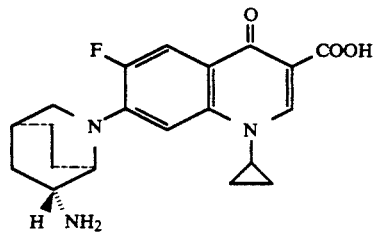

and

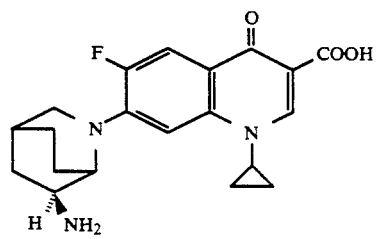

The pharmaceutical compositions of the present invention preferably contain the above preferred and specific preferred compounds.

DETAILED DESCRIPTION OF THE INVENTION

The compounds of formula I may be prepared by reacting a compound of the formula

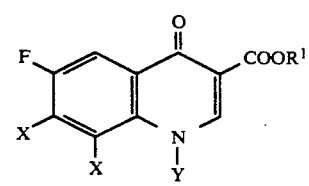

with a compound of the formula $R^2H$ wherein $R^1$, X, Y and $R^2$ are as defined above in connection with formula I, and X is halogen (e.g., fluoro, chloro or bromo).

The reaction may be performed with or without a solvent, preferably at elevated temperature, and for a time sufficient to substantially complete the reaction. The reaction is preferably carried out in the presence of an acid acceptor such as an inorganic or organic base, e.g., an alkali metal or alkaline earth metal carbonate or bicarbonate or a tertiary amine such as triethylamine, pyridine, picoline, or 1,8-diazabicyclo[5.4.0]undec-7-ene (DBU).

The solvents for this reaction are solvents which are non-reactive under the reaction conditions such as acetonitrile, tetrahydrofuran, ethanol, chloroform, dimethylsulfoxide (DMSO), dimethylformamide, pyridine, water, or mixtures thereof.

The reaction temperature usually ranges from about 20° C. to about 150° C.

Starting materials of formula XII are known in the art, e.g., as disclosed in European Patent Application 86307045.4 (Publication No. 0215650).

The starting materials of formula R²H have the following formula

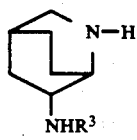

wherein R³ is as defined above. Such compounds may be prepared as shown below.

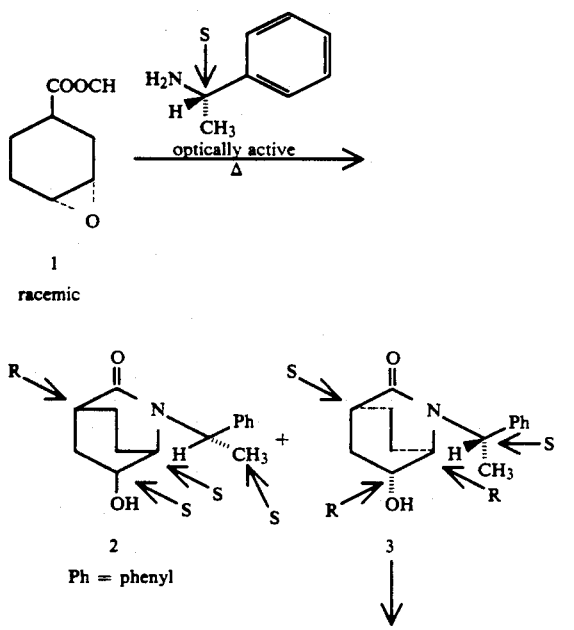

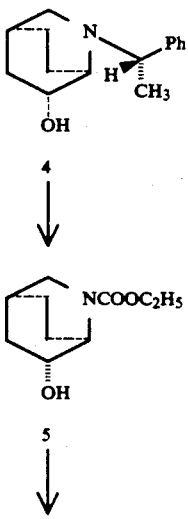

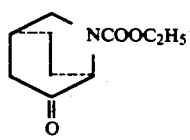

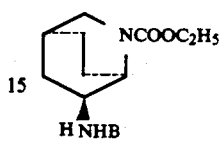 + 

exo          endo
Bn = —CH₂Ph

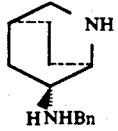

9
dihydrobromide

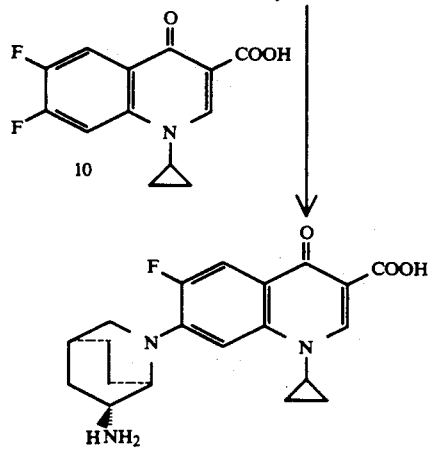

Compounds of the formulae 2 and 3 are prepared analogously in accord with the synthesis of the N-benzyl derivative, (see J. W. Hoffman et al., *J. Org. Chem*, 32, 700 (1967)) in which (S)-(—)-1-phenethylamine is substituted for benzylamine. These compounds are diastereomers and can be separated by silica gel chromatography and/or fractional crystallization. The absolute stereochemistry of 2 and 3 was assigned based on an X-ray crystallographic study of 3. The reaction of 6 with benzylamine followed by reduction produced two diastereomers 7 and 8 which were separated by silica gel chromatography. The relative stereochemistry (exo and endo) of 7 and 8 was assigned by examination of the 1H-NMR hyperfine splitting constants of the proton adjacent to the benzylamino group.

The pharmaceutically acceptable acid addition salts of the compounds of the formula I are prepared in a conventional manner by treating a solution or suspension of the free base of the formula I with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, methanesulfonic, cinnamic, fumaric, phosphonic, hydrochloric, hydrobromic, hydroiodic, sulfamic and sulfonic acid.

The pharmaceutically acceptable cationic salts of the compounds of the formula I may be prepared by conventional methods form the corresponding acids, e.g., by reaction with about one equimolar amount of a base. Examples of suitable cationic salts are those of alkali metals such as sodium or potassium, alkaline earth metals such as magnesium or calcium, and ammonium or organic amines such as diethanol amine or N-methyl-glucamine.

The compounds of formula I and the pharmaceutically acceptable acid addition salts thereof are useful in the treatment of bacterial infections of broad spectrum, particularly the treatment of infections of gram-positive bacterial strains.

The compounds of the present invention may be administered alone, but will generally be administered in a mixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of about 5 to about 5000 ppm, preferably about 25 to about 500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1 to about 50 mg/kg/day, advantageously about 0.2 to about 10 mg/kg/day given in a single daily dose or up to 3 divided doses.

The invention also provides pharmaceutical compositions comprising an antibacterially effective amount of a compound of the formula I or a pharmaceutically acceptable acid addition salt thereof together with a pharmaceutically acceptable diluent or carrier.

The compounds of the present invention can be administered to humans for the treatment of bacterial diseases by either the oral or parenteral routes, and may be administered orally at dosage levels of about 0.1 to about 500 mg/kg/day, advantageously about 0.5 to about 50 mg/kg/day given in a single dose or up to 3 divided doses. For intramuscular or intravenous administration, dosage levels are about 0.1 to about 200 mg/kg/day, advantageously about 0.5 to about 50 mg/kg/day. While intramuscularly administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the compounds of the invention is shown by testing according to the Steer's replicator technique which is a standard in vitro bacterial testing method described by E. Steers et al., *Antibiotics and Chemotherapy*, 9, 307 (1959).

The following non-limiting examples illustrate the invention. All melting points referred to in the Examples are uncorrected. Flash chromatography was performed using 32–63 μm silica gel (Woelm (trademark)) according to the method described by W. C. Still et al., *Journal of Organic Chemistry*, 43, 2923 (1978).

EXAMPLE 1

6-(S)-Hydroxy-2-(1-(S)-phenethyl)-(1S,4R)-2-azabicyclo[2.2.2]octan-3-one and
6-(R)-Hydroxy-2-(1-(S)-phenethyl)-(1R,4S)-2-azabicyclo[2.2.2]octan-3-one Methyl-3-epoxycyclohexyl-1-carboxylate (S. W. Huffman et al., *J. Org. Chem.*, 32, 700 (1967)) (39.56 g, 0.0254 mol) was dissolved in ethanol (200 ml) and placed in a 500 ml round bottom flask. To this stirring solution was added (S)-1-phenethylamine (39.17 ml, 0.304 mol) and the reaction mixture was brought to reflux for 24 hours. The ethanol was then removed in vacuo. The resultant concentrate was heated to 180° C. for 6 hours, cooled, and then dissolved in methanol (60 ml) and 10% aqueous NaOH (60 ml) and this mixture was refluxed for 1 hour. Thereafter, 10% aqueous hydrochloric acid (60 ml) was added to neutralize the sodium hydroxide and the methanol was then removed in vacuo. The organics were redissolved in methylene chloride and washed with hydrochloric acid (50 ml) and brine (100 ml), dried (MgSO$_4$), concentrated and purified by flash chromatography (eluant: 75% ethyl ether/ hexane (25 L), ethyl ether (60 L), and then EtOAc (ethyl acetate) after all the less polar diastereomer was off the column.

The yield of less polar diastereomer (first title compound, compound of formula 2) was 8.25 g (13%). mp 135°–136° C.; $^1$H NMR (CDCl$_3$) δ 1.23(t,1H), 1.31(q,1H), 1.5(d, 3H), 1.75(m, 2H), 2.15(m, 2H}, 2.45(t, 1H), 2.75(s, 1H), 3.35(s, 2H), 5.70(q, 1H), 7.25(m, 5H); $^{13}$C NMR(CDCl$_3$) δ 16.4, 20.7, 24.2, 34.1, 39.1, 48.9, 52.4, 67.8, 127.4, 127.6, 128.5, 140.6, 174.5. Anal. Cal'd for C$_{15}$H$_{19}$NO$_2$: C,73.47; H,7.76; N,5.71; Found: C,73.39; H,7.80; N,5.64.

The yield of more polar diastereomer (second title compound, compound of formula 3 was 11.05 g(18%); mp 178°–179° C.; $^1$H NMR (CDCl$_3$) δ 0.9(t, 1H), 1.30 (s, 1H), 1.38(s, 1H), 1.45(d, 3H), 1.65(m, 2H), 1.9(m, 1H), 2.2(m, 1H), 2.5(s, 1H), 3.36(s, 1H), 3.5(s, 1H), 4.0(s, 1H), 5.8(q, 1H), 7.25(s, 5H); $^{13}$C NMR (CDCl$_3$) δ 16.6 19.4, 24.3, 34.0, 39.1, 48.9, 52.6, 68.9, 127.3, 127.7, 128.5, 140.4, 174.7; Anal. Cal'd for C$_{15}$H$_{19}$NO$_2$: C,73.47; H,7.76; N,5.71; Found: C,73.14; H,7.75; N,6.00.

EXAMPLE 2

6-(S)-Hydroxy-(1-(S)-phenethyl)-(1S,4R)-2-azabicyclo[2.2.2]octane

Lithium aluminum hydride (2.48 g, .0654 mol) was dissolved in freshly distilled THF (tetrahydrofuran) (50 ml) and then the first title compound of Example 1 (8 g, 0.0327 mol) was added in a solution of THF (80 ml) dropwise. Upon completion of the addition, the reaction was brought to reflux for 16 hours. It was then found by TLC (thin layer chromatography) using EtOAc as the eluant, that the reaction was complete. Water (2.48 ml) was then added cautiously, and then 15% aqueous (2.48 ml) was added and finally water (7.5 ml) was added. The salts were filtered off and the organics were concentrated to give the title compound as a white solid. Yield: 6.68 g(89%); mp 141°–143° C.; $^1$H NMR (CDCl$_3$) δ 1.29 (d, 3H), 1.40(m, 1H), 1.56(m, 3H), 1.71(m, 3H), 2.10(t, 1H), 2.55(d, 1H), 2.67(m, 2H), 3.70(q, 1H), 4.15(m, 1H), 7.30(m, 5H); $^{13}$C NMR (CDCl$_3$δ 18.3, 22.9, 24.9, 27.0, 36.4, 50.9, 54.1, 62.7, 67.1, 126.8, 127.4, 128.3; Anal. Cal'd for C$_{15}$H$_{21}$NO: C,77.92; H,9.09; N,6.06; Found: C,77.69; H,9.11; N,6.13.

EXAMPLE 3

6-(R)-Hydroxy-2-(1-(S)-phenethyl)-(1R, 4S)-2-azabicyclo[2.2.2]octane

Lithium aluminum hydride (3.41 g, 0.0898 mol) was dissolved in THF (50 ml) and then the second title compound of Example 1 (11 g, 0.0449 mol) was added in a solution of THF (100 ml) dropwise. Upon completion of the addition, the reaction was brought to reflux for 16 hours. After 16 hours, TLC (eluant: EtOAc) showed that the reaction was complete. Water (3.41 ml), 15% aqueous NaOH (3.4 ml), and water (10.4 ml) were added successively. The salts were then filtered off and the organics were concentrated to an oil which solidified to yield 9.70 g (94%) of the title compound as a white solid, mp 66°–67° C.; $^1$H NMR (CDCl$_3$) δ 1.32(d, 3H), 1.52(m, 2H), 1.76(m, 5H), 2.10(t, 1H), 2.47(m, 2H), 2.90(m, 1H), 3.65(q, 1H), 7.24(m, 5H); $^{13}$C NMR (CDCl$_3$) δ 15.9, 22.6, 25.3, 27.1, 36.1, 51.0, 53.2, 62.6, 68.3, 126.8, 127.3, 128.4, 146.5; Anal. Cal'd for C$_{15}$H$_{21}$NO: C,77.92; H,9.09; N,6.06; Found: C,77.73; H,9.15; N,6.09.

EXAMPLE 4

2-Carboethoxy-6-(S)-hydroxy-(1S,4R)-2-azabicyclo[2.2.2]octane

Pd(OH)$_2$ (3.25 g) was placed into a 500 ml Parr bottle and ethanol (30 ml) was added. The title compound of Example 2 (6.50 g, 0.028 mol) was dissolved in hot ethanol, cooled and then added to the Parr bottle containing the Pd(OH)$_2$. This mixture was shaken under H$_2$ (50 p.s.i.) for 20 hours at which time TLC showed the reaction to be complete. The Pd(OH)$_2$ was then removed by filtration and 12N aqueous HCl (2.33 ml) was added to the ethanol. The ethanol was then removed in vacuo to yield 4.60 g (100%) of the deprotected HCl salt. The deprotected hydrochloride salt (4.60 g, 0.028 mol) was dissolved in 1N aqueous NaOH (120 ml) and then cooled to 0° C. Ethyl chloroformate (4.03 ml, 0.042 mol) was then added dropwise to the stirring solution. The reaction was allowed to stir for 3 hours and the organics were then extracted with EtOAc (4×50 ml). The organic layer was washed with 1N aqueous HCl (50 ml), dried (N$_2$SO$_4$) and concentrated to yield the title compound as a light yellow oil, yield: 5.05 g (90%). $^1$H NMR was the same as for the racemic compound of Example 18.

EXAMPLE 5

2-Carboethoxy-6-(R)-hydroxy-(1R, 4S)-2-azabicyclo[2.2.2]octane

Pd(OH)$_2$ was placed into a Parr bottle and ethanol (30 ml) was added. The title compound of Example 3 (9.50 g, 0.041 mol) was dissolved in hot ethanol (170 ml), cooled, and then added. This mixture was shaken under H$_2$ (50 p.s.i.) for 20 hours at which time TLC (EtOAc) showed the reaction to be complete and the catalyst was then removed by filtration. 12N Aqueous HCl (3.42 ml) was added to the filtrate and then the ethanol removed in vacuo to yield 6.77 g (100%) of deprotected HCl salt. The deprotected hydrochloride salt (6.72 g, 0.041 mol) was dissolved in 1N aqueous NaOH (180 ml) and then cooled to 0° C. Ethyl chloroformate (5.90 ml, 0.062 mol) was added dropwise to the stirring solution. The reaction was allowed to stir for 3 hours and then the organics were extracted with EtOAc (4×50 ml). The combined organic layers were washed with 1N HCl (50 ml), dried (Na$_2$SO$_4$), and concentrated to provide the title compound as a light pink oil, yield: 7.22 g (88%); $^1$H NMR data was the same as that for the racemic compound of Example 18.

EXAMPLE 6

2-Carboethoxy-(1S, 4R)-2-azabicyclo[2.2.2]octan-6-one

The title compound of Example 4 (4.95 g, 0.0249 mol) was dissolved in CH$_2$Cl$_2$(125 ml) and pyridinium chlorochromate (7.15, 0.0332 mol) was added slowly. The reaction mixture was stirred for 17 hours at which time TLC (EtOAc) still showed some starting material present. More pyridinium chlorochromate (1.2 g, 5.57 mol) was therefore added. After 5 hours, TLC showed the reaction to be complete. Concentrated NaHSO$_3$ solution (50 ml) was added and the mixture was filtered through diatomaceous earth (Celite (trademark) and the organic and aqueous layers were separated. The organic layer was washed with H$_2$O (50 ml) and brine (50 ml), dried (Na$_2$SO$_4$) and concentrated to a light green oil which later solidified. The solid (about 4.65 g) was purified by flash chromatography (eluant: EtOAc) to yield a faint green powder which was triturated with EtOAc/hexane to yield 1.75 g (35.7%) of the title compound as a faint green solid, mp 82°–85° C., [α]$_D^{20}$59.4° (CHCl$_3$). $^1$H NMR data was the same as that for the racemic compound of Example 19. Anal. Cal'd. for C$_{10}$H$_{15}$NO$_3$: C,60.91; H,7.61; N,7.11; Found: C,60.89; H,7.67; N,6.98.

EXAMPLE 7

2-Carboethoxy-(1R, 4S)-2-azabicyclo[2.2.2]octan-6-one

The title compound of Example 5 (7.12 g, 0.0358 mol) was dissolved in CH$_2$Cl$_2$ (175 ml) and pyridinium chlorochromate (10.28 g, 0.0477 mol) was added slowly. The reaction mixture was stirred for 16 hours at which time TLC (EtOAc) showed that starting material was still present. Additional pyridinium chlorochromate (2.3 g, 0.011 mol) was added and the reaction mixture was stirred an additional 5 hours. Concentrated NaHSO$_3$ solution (75 ml) was added and reaction mixture was filtered over diatomaceous earth (Celite (trademark)) and the layers were separated. The organic layer was washed with water (50 ml) and brine (50 ml), dried (Na$_2$SO$_4$), and concentrated to a light green oil which solidified to a green solid. This solid (about 5.8 g) was purified by flash chromatography (eluant: EtOAc) to yield 5.5 g of a white solid which was triturated (EtOAc/hexane) to give 3.95 g (56%) of the title compound, mp 82°–85° C.; [α]$_D^{20}$−56.4° (CHCl$_3$); Anal, Cal'd for C$_{10}$H$_{15}$NO$_3$: C,60.91; H,7.61; N,7.11; Found: C,60.94; H,7.63; N,7.02. $^1$H NMR data was the same as that of the racemic compound of Example 19.

EXAMPLE 8

6-(S)-Benzylamino-2-carboethoxy-(1S, 4R)-2-azabicyclo [2.2.2]octane, and 6-(R)-Benzylamino-2-carboethoxy(1S, 4R)-2-azabicyclo[2.2.2]octane The title compound of Example 6 (2 g, 0.010 mol) was dissolved in benzene (60 ml). Benzylamine (1.22 ml, 0.011 mol) was added and the mixture was heated to reflux for 24 hours as the apparatus was equipped with a Dean-Stark trap to remove $H_2O$. After 24 hours, the benzene was removed in vacuo and the residue was cooled to 0° C., diluted with ethanol (80 ml), and then treated with $NaBH_4$ (1.92 g, 0.051 mol) in small portions. After 3 hours, 1N aqueous HCl (55 ml) was added to the flask very slowly. The ethanol was removed in vacuo and replaced with EtOAc. The layers were separated and the aqueous layer was brought to pH 14 and was extracted with EtOAc (2×50 ml). The EtOAc layer was dried ($Na_2SO_4$), concentrated to a clear oil, and the resultant oil (2.4 g) was purified by flash chromatography (eluant: EtOAc). The less polar material (first title compound) weighed 0.83 g (28%), $[\alpha]_D^{20} 22.9°(CHCl_3)$. The NMR data was the same as that for the racemic compound 20A of Example 20. The more polar material (second title compound) weighed 0.43 g (14.7%), $[\alpha]_D^{20} 6.2°(CHCl_3)$. $^1H$ NMR data was the same as that for the racemic compound 20B of Example 20.

EXAMPLE 9

6-(R)-Benzylamino-2-carboethoxy-(1R, 4S)-2-azabicyclo [2.2.2]octane, and 6-(S)-Benzylamino-2-carboethoxy(1R, 4S)-2-azabicyclo[2.2.2]octane The title compound of Example 7 (2.1 g, 0.0107 mol) was dissolved in benzene (60 ml) and benzylamine (1.28 ml, 0.012 mol) was added. The mixture was heated to reflux for 24 hours using a Dean-Stark trap to remove $H_2O$. After 24 hours, the benzene was removed in vacuo. The residue was cooled to 0° C. and diluted with ethanol (50 ml), and treated with $NaBH_4$ (2.03 g, 0.053 mol) in small portions. After 3 hours, 1N aqueous HCl (55 ml) was added to the flask very slowly. The ethanol was removed in vacuo and was replaced with EtOAc. The layers were separated and the aqueous layer was brought to pH 14, and the organics were extracted with EtOAc (2×50 ml). The combined EtOAc layers were dried ($Na_2SO_4$), concentrated to a clear oil (about 2.2 g), and purified by flash chromatography (eluant: EtOAc). The yield of less polar material (first title compound) was 1 g (32%), $[\alpha\pi_D^{20} -22.4°$ $(CHCl_3)$. The NMR data was the same as that for the racemic compound 20A of Example 20. The more polar material (second title compound) weighted 0.50 g (16%), $[\alpha]_D^{20} -5.3°(CHCl_3)$. The NMR data was the same as for the racemic compound 20B of Example 20.

EXAMPLE 10

6-(R)-Benzylamino-(1S, 4R)-1-azabicyclo[2.2.2]octane Dihydrobromide

The second title compond of Example 8 (0.40 g, 1.39 mmol) was dissolved in 48% aqueous HBr (8 ml)) and was heated to reflux for 2.5 hours. The solvent was then removed via a water aspirator and residual water was removed via an azeotrope formed with isopropyl alcohol. The title compound was then obtained after triturating the residue in ethyl ether. Yield: 0.525 g (100%); $[\alpha]_D^{20} 31.2°(H_2O)$; mp 271°-274° C.; Anal. Cal'd for $C_{14}H_{22}N_2Br_2$: C,44.44; H,5.82; N,7.41; Found: C,44.58; H,5.85; N,7.16. NMR data was the same as that of the racemic compound of Example 23.

EXAMPLE 11

6-(S)-Benzylamino-(1R, 4S)-2-azabicyclo[2.2.2]octane Dihydrobromide

The second title compound of Example 9 (0.41 g, 1.39 mmol) was dissolved in 48% aqueous HBr and was heated to reflux for 2.5 hours. The solvent was removed via a water aspirator and residual water was removed via an azetrope with isopropyl alcohol. The title compound was then obtained by triturating the residue with ethyl ether to yield 0.50 g (93%) of a tan solid; $[\alpha]_D^{20} -35.6°(H_2O)$; mp 270°-274° C.; Anal. Cal'd for $C_{14}H_{22}N_2Br_2$: C,44.44; H,5.82; N,7.41; found: C,44.24; H,5.87; N,7.32. The NMR data was the same as that of the racemic compound of Example 23.

EXAMPLE 12

6-(S)-Benzylamino-(1S, 4R)-2-azabicyclo[2.2.2]octane Dihydrobromide

The first title compound of Example 8 (0.72 g, 2.50 mmol) was dissolved in 48% aqueous HBr (10 ml) and was then heated to reflux for 2 hours. The solvent was removed under a steady stream of $N_2$, and residual water was removed with an isopropyl alcohol azotrope. The salt was then triturated in ethyl ether yielding 0.940 g (94%) of the title compound; mp 241°-245° C.; $[\alpha]_d^{20} 27.0°(H_2O)$; Anal. Cal'd for $C_{14}H_{22}N_2Br_2$: C,44.44; H,5.82; N,7.41; Found: C,44.28; H,5.79; N,7.39. The NMR data was the same as that of the racemic compound of Example 21.

EXAMPLE 13

6-(R)-Benzylamino-(1R, 4S)-2-azabicyclo[2.2.2]octane Dihydrobromide

The first title compound of Example 9 (0.78 g, 2.71 mmol) was dissolved in 48% aqueous HBr (10 ml) and was heated to reflux for 2 hours. The solvent was then evaporated under a steady stream of $N_2$ and residual water was removed via an azeotrope with isopropyl alcohol. The resulting salt was triturated in ethyl ether yielding 1 g (98%) of the title compound, mp 241°-245° C.; $[\alpha]_D^{20} -31.5°(CHCl_3)$. Anal Cal'd for $C_{14}H_{22}N_2Br_2$: C,44.44; H,5.82; N,7.41; Found: C,44.40; H,5.62; N,7.24. NMR data was the same as for racemic compound of Example 21.

EXAMPLE 14

7-(6-(R)-Amino-(1S, 4R)-2-azabicyclo[2.2.2]oct-2-yl)-1-cyclopropyl-1,4-dihydro-6-fluoro-4-oxo-3quinoline carboxylic Acid 1-Cyclopropyl-6,7-difluoro-1,4-dihydro-4-oxo-3-quinolinecarboxylic acid (0.5189 g, 1.96 mmol) and the compound of Example 10 (0.543 g, 1.44 mmol) were dissolved in pyridine (10 ml). DBU (0.542 ml, 2.5 eq.) was then added and the mixture was heated to 70° C. for 17 hours. The pyridine was then removed in vacuo and the resulting brown solid was purified by flash chromatography (90 g of silica gel; eluant: 5% methanol/$CHCl_3$) to give 0.58 g of a yellow solid. The solid was dissolved in methanol (70 ml) and was added to a Parr bottle containing $Pd(OH)_2$ (0.70 g) and methanol (5 ml). The mixture was shaken under H$_2$(45 p.s.i.) for 3 hours, filtered through diatomaceous earth (Celite (trademark)), and concentrated. The filtrate was crystallized from methanol/CHCl$_3$ and was further purified by flash chromatography using a 5 minimum amount of silica gel (5 g of silica gel; eluant: 2%–5% methanol/CHCl$_3$) to yield 45 mg of the title compound as a white solid, after trituration with methanol/CHCl$_3$; $[\alpha]_D^{20}$23.7°(DMSO), mp 310° C. NMR was the same as for the racemic compound of Example 24.

EXAMPLE 15

7-(6-(S)-Amino-(1R, 4S)-2-azabicyclo[2.2.2]oct-2-yl)-1-cyclopropyl-1,4-dihydro-6-fluoro-4-oxo-3-quinoline carboxylic Acid In a manner similar to that of Example 14, the title compound of Example 11 (0.41 g) was coupled to 1-cycloropyl-6,7-difluoro-1,4-dihydro-4-oxo-3-quinoline carboxylic acid in the presence of DBU, and the product was subjected to catalytic hydrogenation to remove the benzyl group, yielding 30 mg of the title compound as a light yellow solid, mp 310°, $[\alpha]_D^{20}$−43.4°(DMSO). NMR data was the same as for the racemic compound of example 24.

EXAMPLE 16

7-(6-(S)-Amino-(1S, 4R)-2-azabicyclo[2.2.2]oct-2-yl)-1cyclopropy-1,4-dihydro-6-fluoro-4-oxo-3-quinoline carboxylic Acid In a manner similar to that of Example 14, the title compound of Example 12 (0.80 g) was coupled to 1-cyclopropyl-6,7-difluoro-1,4-dihydro-4-oxo-3-quinoline carboxylic acid in the presence of DBU, and the product was similarly subjected to catalytic hydrogenation to remove the benzyl group, yielding 0.24 g of the title compound, mp 267°–270°, $[\alpha]_D^{20}$66.3°(DMSO). NMR data was the same as for the racemic compound of Example 22.

EXAMPLE 17

7-(6-(R)-Amino-(1R, 4S)-2-azabicyclo[2.2.2]oct-2-yl)-1-cyclopropyl-1,4-dihydro-6-fluoro-4-oxo-3-quinoline carboxylic Acid In a manner similar to that of Example 14, the title compound of Example 13 (0.80 g) was coupled to 1-cyclopropyl-6,7-difluoro-1,4-dihydro-4-oxo-3-quinoline carboxylic acid in the presence of DBU and the product was subjected to catalytic hydrogenation to remove the benzyl group, yielding 0.16 g of the title compound as a solid, mp 268°–271°, $[\alpha]_D^{20}$−69.3°(DMSO). NMR data was the same as for the racemic compound of Example 22.

EXAMPLE 18 endo-2-Carboethoxy-6-hydroxy-2-azabicyclo[2.2.2]octane

A mixture of 22.02 g (101.3 mmol) of 2-benzyl-6-endo-hydroxy-2-azabicyclo[2.2.2]octane (R. F. Borne et al., *J. Het. Chem.*, 10, 241 (1973), 16.88 ml (202.6 mmol) of 12M aqueous hydrochloric acid solution, 5.00 g of Pd(OH)$_2$, and 370 ml of absolute ethanol was hydrogenated for 16 hours at 40 psi on a Parr shaker apparatus. An additional 5.00 g of Pd(OH)$_2$ was then added and hydrogenation was continued for 24 hours. The mixture was filtered through diatomaceous earth (Celite (trademark)) and the ethanol was removed by rotary evaporation. The solid residue (24 g) was diluted with 200 ml of 2N aqueous sodium hydroxide solution and was treated dropwise at 0° C. with 16.49 g (152 mmol) of ethyl chloroformate. After 1 hour of stirring, the mixture was extracted with EtOAc (4×100 ml) and the dried (MgSO$_4$) extracts were evaporated to 20.06 g (99%) of the title compound (Rf 0.3, EtOAc) as an oil: $^1$H NMR (300 MHz, CDCl$_3$) δ 1.16–1.27 (m, 3H), 2.4–2.8 (broad S, 1H) 3.14–3.25 (m, 2H), 3.85–4.20 (m, 4H).

EXAMPLE 19

2-Carboethoxy-2-azabicyclo(2.2.2)octan-6-one

To a solution of 20.00 g (100 mmol) of the title compound of Example 18 in 700 ml of dichloromethane was added 32.46 g (150 mmol) of pyridinium chlorochromate in small portions. The mixture was stirred for 5.5 hours at which time it was washed with 10% aqueous NaHSO$_4$ solution (4×200 ml) and water (2×200 ml), dried (MgSO$_4$), and evaporated to 22.5 g of an oil. Purification of the oil by flash chromatography with a 1% methanol/CHCl$_3$ eluant gave an oil which was crystallized from pentane to afford 14.23 g of 2-carboethoxy-2-azabicyclo[2.2.2]octan-6-one (Rf 0.75, 10% methanol/CHCl$_3$), mp 68.5°–69.5° C.: $^1$H NMR (300 MHz, CDCl$_3$) δ 1.18–1.26 (m, 3H), 1.52–1.81 (m, 2H), 1.90 (t, 1H, J=12), 2.05–2.20(m, 1H), 2.30–2.33 (m, 3H), 3.39–3.52 (m, 2H), 4.02–4.40 (m, 3H); mass spectrum m/e 197(M+), 169,140 (base).

EXAMPLE 20 endo and exo-6-Benzylamino-2-carboethoxy-2-azabicyclo[2.2.2]octane

To a mixture of 350 mg (1.8 mmol) of the title compound of Example 19, 246 mg (2.3 mmol) of benzylamine, 108 mg of acetic acid (1.8 mmol), and 8 ml of methanol, was added 453 mg (7.2 mmol) of sodium cyanoborohydride. As the mixture was allowed to stir at room temperature, it was adjusted periodically to pH 6 by the addition of acetic acid. After 16 hours of stirring, the solvent was removed and to the solid residue was carefully added 25 ml of aqueous 1N HCl solution until the gas evolution (hydrogen cyanide!) had ceased. The acidic mixture was washed with EtOAc (2×50 ml), basified to pH 12, and extracted with EtOAc (2×50 ml). The combined extracts were dried (K$_2$CO$_3$) and evaporated to 459 mg of an oil. Separation of the oil by flash chromatography using a 2.5% methanol/CHCl$_3$ eluant gave 197 mg (38%) of endo-6-benzylamino-2-carboethoxy-2-azabicyclo[2.2.2]octane as an oil (compound 20A) (Rf 0.55, 10% methanol/CHCl$_3$): $^1$H NMR (250 MHz, CDCl$_3$) 1.56 and 1.55 (two t, 3H, J=7), 1.13–1.25 (m, 1H), 1.50–1.82 (m, 3H), 1.82–2.14 (m, 3H), 2.98–3.13 (m, 1H), 3.23–3.38 (m, 2H), 3.78 (centroid of AB pattern, 2H, J=14), 3.94–4.17 (m, 1H), 4.12 (q, 2H, J=7), 7.21–7.38 (m, 5H). Later fractions gave 84 mg (16%) of exo-6-benzylamino-2-carboethoxyazabicyclo[2.2.2]octane as an oil (compound 20B) (Rf 0.43, 10% MeOH/CHCl$_3$): $^1$H NMR (250 MHz, CDCl$_3$) δ 1.13–1.28 (m, 1H), 1.25 (t, 2H, J=7), 1.42–1.63 (m, 3H), 1.85–2.11 (m, 3H), 2.82–2.92 (m, 1H), 3.25–3.44 (m, 2H), 3.80 (centroid of ABX pattern, 2H, J$_{AB}$=15, J$_{AX}$=10, J$_{BX}$=4), 4.18 and 4.19 (two q, 2H, J=7), 4.18–4.30 (m, 1H), 7.21–7.39 (m, 5H).

EXAMPLE 21 endo-6-Benzylamino-2-azabicyclo[2.2.2]octane Dihybromide

A mixture of 186 mg (0.64 mmol) of compound 20A and 2 ml of aqueous 48% HBr solution was heated to reflux for 2 hours. The solvent was removed by distillation (aspirator vacuum) and the residue was azeotroped with isopropanol, leaving behind a white powder which was triturated with ether to afford 244 mg (92%) of the title compound. $^1$H-NMR (250 MHz, D$_2$O) 1.73–2.20(m,5H), 2.25(S,1H), 2.45(1H, broad t), 3.20–3.40(m,1H), 3.85–3.95(m,2H), 4.41(centroid of AB quartet, 2H,J=14); $^{13}$C-NMR (63 MHz, D$_2$O) δ 17.2, 22.2, 23.0, 28.4, 45.2, 45.4, 50.7, 51.8, 130.3, 130.6, 130.9, 131.1.

EXAMPLE 22 endo-7-(6-Amino-2-azabicyclo[2.2.2]oct-2-yl)-1-cyclopropyl-1,4-dihydro-6-fluoro-4-oxo-3-quinolinecarboxylic Acid A mixture of 2.36 g (6.2 mmol) of the title compound of Example 21, 1.97 g (6.9 mmol) of 1-cyclopropyl-6,7-difluoro-1,4-dihydro-4-oxo-3-quinoline carboxylic acid, 2.30 g (15.5 mmol) of DBU and 20 ml of pyridine was heated for 16 hours under N$_2$ at 70° C. The solvent was removed and the oily residue was purified by flash chromatography with a 4% methanol-CHCl$_3$ eluant to give 3.16 g of a mixture of endo 7-(6-benzylamino-2-azabicyclo[2.2.2]oct-2-yl)-1-cyclopropyl-1,4-dihydro-6-fluoro-4-oxo-3-quinoline carboxylic acid (Rf 0.39, 18:2:1 CHCl$_3$: MeOH: acetic acid) and unreacted 1-cyclopropyl-6,7-difluoro-1,4-dihydro-4-oxo-3-quinoline carboxylic acid. This mixture was then hydrogenated in 350 ml of methanol in the presence of 3.5 g of Pd(OH)$_2$ at 50 p.s.i. on a Parr shaker apparatus for 2.5 hours. The mixture was filtered and the residue was concentrated to 2.01 g of a yellow solid which was purified by flash chromatography with a 10% methanol-CHCl$_3$ eluant to give 0.98 g of a yellow solid. Trituration of the yellow solid in hot EtOAc/isopropanol afforded 0.530 g (18%) of the title compound as a light yellow powder, mp 255°–257° C.: $^1$H-NMR (250 MHz, DMSO d$^6$) δ 1.00–2.35 (m, 10H), 4.30–4.44, 4.30–4.45 (m, 1H); 7.27 (broad d, 1H), 7.83 (d, 1h, J=13), 8.58 (S, 1H); high resolution mass spectrum, calc'd for C$_{20}$H$_{22}$FN$_3$O$_3$ m/e 371.1646, found m/e 371.1662.

EXAMPLE 23 exo-6-Benzylamino-2-azabicyclo[2.2.2]octane Dihydrobromide

A mixture of 76 mg (0.26 mmol) of compound 20B and 2 ml of aqueous 48% HBr solution was heated to reflux for 2 hours. The solvent was removed by distillation (aspirator vacuum) and the residue was azeotroped with isopropanol leaving behind a white solid which was triturated with ether to afford 98 mg (99%) of the title compound, $^1$H-NMR (300 MHz, D$_2$O) δ 1.68–2.32 (m, 6H), 2.55 (broad t, 1H), 3.28–3.44 (m, 2H), 3.80–3.89 (1H, m), 3.95 (S, 1H) 4.38 (centroid of AB pattern, 2H, J=14), 7.53 (S, 5H: $^{13}$C-NMR (63 Mz, D$_2$O) 21.1, 22.4, 22.9, 28.3, 46.1, 47.0, 50.3, 53.9, 130.3, 130.7, 10, 130.8, 130.9.

EXAMPLE 24 exo-7-(6-Amino-2-azabicyclo[2.2.2]oct-2-yl)-1-cyclopropyl-1,4-dihydro-6-fluoro-4-oxo-3-quinolinecarboxylic Acid A mixture of 160 mg (0.42 mmol) of the title compound of Example 23, 133 mg (0.50 mmol) of 1-cyclopropyl-6,7-difluoro-1,4-dihydro-4-oxo-3-quinoline carboxylic acid, 0.257 g (1.68 mmol) of DBU, and 4 ml of pyridine was heated to 40° C. for 56 hours under N$_2$ The solvent was removed and the oily residue was purified by flash chromatography using a 2.5–5% methanol/CHCl$_3$ eluant to provide 128 mg of exo-7-(6-benzylamino-2-azabicyclo[2.2.2]oct-2-yl)-1-cyclopropyl-1,4-dihydro-6-fluoro-4-oxo-3-quinolinecarboxylic acid (Rf 0.2, 18:2:1 CHCl$_3$: methanol:acetic acid) as a yellow solid which was then hydrogenated at 40 p.s.i. in 50 ml of methanol in the presence of 100 mg of Pd(OH)$_2$. The catalyst was filtered and the filtrate was evaporated to a 86 mg of a yellow solid which, after trituration with isopropanol, there was obtained 36 mg (23%) of the the title compound (Rf 0.05, 18:2:1 CHCl$_3$: methanol: acetic acid) as a tan solid, mp 234°–240° C.: $^1$H-NMR (300 MHz, DMSO d$_6$) δ 4.20–4.50 (m, 1H), 7.32 (broad d, 1H), 7.80 (d, J=13, 1H), 8.59 (2, 1H); high resolution mass spectrum, calc'd for C$_{20}$H$_{22}$FN$_3$O$_3$ m/e 371.1655, found m/e 71.1670.

EXAMPLE 25 endo-7-(6-Amino-2-azabicyclo[2.2.2]oct-2-yl)-1-cyclopropyl-6,8-difluoro-1,4-dihydro-4-oxo-3-quinolinecarboxylic Acid A mixture of 290 mg (0.76 mmol) of compound 20A, 215 mg (0.76 mmol) of 1-cylopropyl-6,8-difluoro-1,4-dihydro-4-oxo-3-quinolinecarboxylic acid, 289 mg (1.89 mmol) of DBU, and 5 ml of pyridine was heated to 70° C. under N$_2$ for 16 hours. The solvent was removed and the residue was purified by flash chromatography using a 10% methanol/CHCl$_3$ eluant to give 283 mg of a mixture of 7-(6-benzylamino-2-azabicyclo[2.2.2]oct-2-yl)-1-cyclopropyl-6,8-difluoro-1,4-dihydro-4-oxo-3-quinolinecarboxylic acid and unreacted 1-cyclopropyl-6,8-difluoro-1,4-dihydro-4-oxo-3-quinolinecarboxylic acid. The mixture was then hydrogenated at 50 p.s.i. in 50 ml of methanol in the presence of 100 mg of Pd(OH)$_2$ for 1.5 hours. The catalyst was removed by filtration and the solvent was evaporated to an oil which was purified by flash chromatography using a 10% methanol/CHCl$_3$ eluant to afford 27 mg (10%) of the title compound (Rf 0.08, 18:2:1 CHCl$_3$: methanol: acetic acid) as a light yellow solid, mp 251°–253° C.; $^1$H NMR (300 MHz, CDCl$_3$) δ 0.64–0.84 (m, 1H), 0.98–1.35 (5H, m), 2.67 (broad S, 2H), 1.80–2.30 (m, 4H), 3.16–3.69 (m, 5H), 3.84–3.98 (M, 1H), 7.70 (broad d, 1H), 8.64 (s, 1H); high resolution mass spectrum, calc'd for C$_{20}$H$_{21}$F$_2$N$_3$O$_3$ m/e 389.1579, found 389.1565.

EXAMPLE 26 endo-2-Benzyloxycarbonyl-6-hydroxy-2-azabicyclo[2.2.2]octane

A mixture of 5.6 g (25.8 mmol) of endo-2-benzyl-6-hydroxy-2-azabicyclo[2.2.2]octane, 120 ml of absolute ethanol, 10 ml of concentrated aqueous HCl solution, and 2.8 g of 10% Pd/C was hydrogenated at 50 p.s.i. for 48 hours. During the hydrogenation, at 16 hours and 20 hours, additional amounts of catalyst (1.0 g each addition) and concentrated aqueous HCl solution (10 equivalents and 6 equivalents, respectively) were added. Filtration of the catalyst, evaporation of the filtrate, and crystallization of the residue from isopropanol gave a white solid which was dissolved in 60 ml of water. The mixture was then basified to pH 10 with solid $K_2CO_3$, chilled to 0° C., and treated with 5.88 g (34.4 mmol) of benzylchloroformate. After stirring 16 hours with slow warming to room temperature, the mixture was extracted with EtOAc (3×100 ml). The combined extracts were dried ($K_2CO_3$) and evaporated to 7 g of an oil which was purified by flash chromatography using a 1:1 EtOAc: hexane eluant to provide 6.09 g (90%) of the title compound (Rf 0.27, 1:1 EtOAc: hexane) as an oil; $^1$H-NMR (300 MHz, CHCl$_3$) δ 1.30-2.20 (m, 8H), 3.20-3.36 (m, 2H), 3.95-4.12 (m, 2H), 5.12 (s, 2H), 7.23-7.40(m, 5H).

EXAMPLE 27

2-Benzyloxycarbonyl-2-azabicyclo[2.2.2]octan-6-one

A solution of 6.00 g (2.30 mmol) of endo-2-benzyloxycarboxyl-6-hydroxy-2-azabicyclo[2.2.2]octane in 45 ml of acetone was to chilled 0° C. and was treated dropwise with 10.0 ml (26.7 mmol) of Jones reagent (K. Bowden et al., *J. Chem. Soc.*, 39 (1946)). After stirring 2 hours, the solvent was removed by evaporation and the residue was diluted with 50 ml of water and was extracted with EtOAc (2×50 ml). The combined EtOAc extracts were washed with water (2×50 ml), and saturated aqueous NaHCO$_3$ solution (2×30 ml), dried ($K_2CO_3$), and evaporated to 4.20 g (70%) of 2-benzyloxycarbonyl-2-azabicyclo[2.2.2]octan-6-one as an oil (Rf 0.46, 1:1 EtOAC: hexane); $^1$H-NMR (300MHz, CDCl$_3$) δ 1.55-1.80 (m, 4H), 1.83-1.99 (m, 2H), 2.06-2.24 (m, 2H), 2.32-2.45 (m, 2H), 2.40 (s, 1H), 3.42-3.56 (m, 2H), 4.26-4.33 (m, 1H), 5.11 (centroid of AB pattern, 2H, J=15), 7.25-7.38 (m, 5H).

EXAMPLE 28 endo and exo-6-Benzylamino-2-benzyloxycarbonyl-2azabicyclo[2.2.2]octane

To a mixture of 4.05 g (15.6 mmol) of the title compound of Example 27, 1.70 g (15.9 mmol) of benzylamine, 0.94 g (15.6 mmol) of acetic acid in 50 ml of methanol was added 3.92 g (62.4 mmol) of sodium cyanoborohydride. The mixture was allowed to stir 16 hours as minimum amounts of additional acetic acid were added to maintain the pH at 6. The solvent was removed by evaporation and the semi-solid residue was carefully treated with 200 ml of aqueous 2N HCl solution (HCN evolution!). Following 45 minutes of additional stirring, the mixture was washed with ether (3×100 ml), basified to pH 14 with aqueous 4N NaOH solution, and extracted several times with EtOAc. The combined EtOAc extracts were dried ($K_2CO_3$) and evaporated to 2.2 g of an oil which was separated by flash chromatography using an EtOAC eluant to afford 675 mg (12%) of the less polar endo diastereomer of the title compound as an oil (Rf 0.32, EtOAc) and 310 mg (6%) of the more polar exo diastereomer of the title compound as an oil (Rf 0.18, EtOAc). The $^1$H-NMR (300 MHz, CDCl$_3$) of the mixture of diastereomers showed two singlets (2H each) at δ 3.85 and 5.16.

EXAMPLE 29 endo-6-Benzylethylamino-2-benzyloxycarbonyl-2-azabicyclo[2.2.2]octane

A mixture of 500 mg (1.4 mmol) of endo-6-benzylamino-2-benzyloxycarbonyl-2-azabicyclo[2.2.2]octane, 5 ml of DMF, 5 ml of benzene, 592 mg (4.2 mmol) of $K_2CO_3$, and 240 mg (1.54 mmol) of ethyliodide was stirred for 4 days at 60° C. Additional ethyl iodide (1 equivalent) was added on the third day as the course of the reaction was monitored by TLC. The solvent was removed by evaporation and the residue was extracted with EtOAc, filtered, and evaporated to an oil which was purified by flash chromatography using an EtOAc eluant to afford 390 mg (72%) of the title compound as an oil (Rf 0.75, EtOAc); $^1$H-NMR (300 MHz, CDCl$_3$) δ 0.81 (m, 3H), 1.44-1.80 (m, 4H), 1.80-2.15 (m, 3H), 2.64 (q, 2H, J=7), 2.81-2.97 (m, 2H), 3.37 (s, 2H), 3.44-3.78 (m, 2H), 4.19-4.32 (m, 1H), 5.08-5.24 (m, 2H), 7.13-7.42 (m, 10H).

EXAMPLE 30 endo-6-Benzylethylamino-2-azabicyclo{2.2.2]octane Dihydrobromide

A mixture of 250 mg (0.66 mmol) endo-6-benzylethylamino-2-benzyloxycarbonyl-2-azabicyclo[2.2.2] octane and 2.5 ml of aqueous 48% HBr solution was allowed to stand for 16 hours at room temperature. The solvent was removed by evaporation and the residue was co-evaporated several times with isopropanol to afford, after trituration in ether, 128 mg (47%) of the title compound; $^1$H-NMR (250 MHz, D$_2$)) δ 1.41(t, 3H, J=6), 1.72-2.26 (m, 5H), 2.32 (s, 1H), 2.50-2.69 (m, 1H), 3.11-3.43 (m, 4H), 3.93 (broad t, 1H), 4.16 (s, 1H), 7.44-7.68 (m, 5H).

EXAMPLE 31 endo-1-Cyclopropyl-1,4-dihydro-7-(6-ethylamino-2-azabicyclo[2.2.2]oct-2-yl)-6-fluoro-4-oxo-3-quinolinecarboxylic Acid A mixture of 100 mg (0.25 mmol) of endo-6-benzylethyl-amino-2-azabicyclo[2.2.2]octane dihydrobromide, 67 mg (0.26 mmol) of 1-cyclopropyl-6,7-difluoro-1,4-dihydro-4-oxo-3-quinoline carboxylic acid, 152 mg (1.00 mg) of DBU, and 4 ml of pyridine was heated to 70° C. for 16 hours. The solvent was removed by evaporation and the residue was crystallized from methanol. The solid was filtered and the mother liquor was purified by flash chromatography using a 10% methanol/CHCl$_3$ eluant to provide a total (combined with parent solid) of 38 mg (32%) of endo-7-(6-benzylethyl-amino-2-azabicyclo[2.2.2]oct-2-yl)-1-cyclopropyl-1,4-dihydro-6-fluoro-4-oxo-3-quinoline carboxylic acid (Rf 0.25, 18:2:1 CHCl$_3$: MeOH: HOAc). The product was dissolved in 20 ml of methanol and was hydrogenated in the presence of 40 mg of Pd(OH)$_2$ at 50 p.s.i. on a Parr Shaker apparatus for 3.5 hours. Filtration of the catalyst, evaporation of the solvent, and purification of the residue by flash chromatography using a 10% methanol/CHCl$_3$ eluant provided 6 mg (16%) of the title compound (Rf 0.05, 18:2:1, CHCl$_3$: methanol: acetic acid) as a solid, mp 230° C. (dec.); $^1$H-NMR(300 MHz, CDCl$_3$) δ 1.18(t, 3H, J=6), 1.95(broad t, 1H), 2.73(q, 2H, J=6), 4.12-4.16(m, 1H), 6.98(d, 1H, J=7), 7.83(d, 1H, J=13), 8.59(s, 1H); high resolution mass spectrum, calc'd for $C_{22}H_{26}FN_3O_3$ m/e 399.1958, found 399.1978.

EXAMPLE 32 exo-6-Benzylethylamino-2-benzyloxycarbonyl-2-azabicyclo[2.2.2]octane

A mixture of 250 mg (0.7 mmol) of exo-6-benzylamino-2-benzyloxycarbonyl-2-azabicyclo[2.2.2]octane, 296 mg (2.1 mmol) of $K_2CO_3$, 5 ml of benzene, 5 ml of DMF, and 120 mg (0.77 mmol) of ethyl iodide was heated to 60° C. for 7 days. Additional ethyl iodide (4 equivalents) was added on each of the first four days as the course of the reaction was monitored by TLC. The solvent was removed by evaporation and the residue was extracted with EtOAC, filtered, and evaporated to an oil which was purified by flash chromatography using a 1:1 EtOAc: hexane eluant to afford 200 mg (74%) of the title compound as an oil (Rf 0.57, EtOAc); $^1$H-NMR (300 MHz, $CDCl_3$) δ 0.87 and 0.94 (two t, 3H, J=7), 1.43–1.62(m, 4H), 1.75–2.01(m, 3H), 2.43–2.72(m, 2H), 2.82–2.96(m, 1H), 3.29–3.85(4H), 4.22–4.38(m, 1H), 5.05–5 24(m, 2H), 7.14–7.38(m, 10H).

EXAMPLE 33 exo-6-Benzylethylamino-2-azabicyclo[2.2.2]octane Dihydrobromide

A mixture of 200 mg (0.5 mmol) of exo-6-benzylethylamino-2-benzyloxycarbonyl-2-azabicyclo[2.2.2] octane and 2 ml of aqueous 48% HBr solution was stirred for 16 hours at room temperature. The solvent was removed by evaporation and the residue was co-evaporated several times with isopropanol to a solid which was triturated in ether to afford 142 mg (66%) of the title compound; $^1$H-NMR(250 MHz, $D_2O$) δ 1.31(t, 3H, J=6), 1.63–2.29(m, 5H), 2.38(s, 1H), 2.60–2.81(m, 2H), 3.16–3.49(m, 4H), 4.03(broad t, 1H), 4.24(broad s, 1H), 7.51–7.66(m, 5H).

EXAMPLE 34 exo-1-Cyclopropyl-1,4-dihydro-7-(6-ethylamino-2azabicyclo[2.2.2]oct-2-yl)-6-fluoro-4-oxo-3-quinoline carboxylic Acid A mixture of 120 mg (0.30 mmol) of exo-6-benzylethylamino-2-azabicyclo[2.2.2]octane dihydrobromide, 95 mg (0.36 mmol) of 1-cyclopropyl-6,7-difluoro-1,4-dihydro-4-oxo-3-quinolinecarboxylic acid, 182 mg (1.20 mmol) of DBU, and 4 ml of pyridine was stirred for 16 hours at 70° C. The solvent was removed by evaporation and the residue was purified by flash chromatography using a 3% acetic acid, 7% methanol in $CHCl_3$ eluant to provide 134 mg of the acetic acid salt of exo-7-(benzylethylamino-2-azabicyclo[2.2.2]oct-2-yl)-1-cyclopropyl-1,4-dihydro-6-fluoro-4-oxo-3-quinolinecarboxylic acid as the acetic acid salt. The free base was obtained by treating the salt with saturated aqueous $NaHCO_3$ solution, extraction with $CHCl_3$, drying ($K_2CO_3$), and evaporation. The free base was then hydrogenated in 20 ml of methanol at 50 p.s.i. in the presence of 50 mg of $Pd(OH)_2$ on a Parr shaker apparatus for 4 hours. The catalyst was removed by filtration and the filtrate was concentrated to an oil which was purified by flash chromatography using a 20% methanol/$CHCl_3$ eluant to afford 31 mg (45%) of the title compound (Rf 0.05, 18:2:1 $CHCl_3$:MeOH:AcOH) as a solid, mp 159°–161° C.; $^1$H-NMR(300 MHz, $CDCl_3$) δ 1.10–1.50(m, 7H), 3.42(s, 1H), 4.50–4.67(m, 1H), 6.98(d, 1H, J=7), 7.62(d, 1H, J=13), 8.27(s, 1H); high resolution mass spectrum, calc'd for $C_{22}H_{26}FN_3O_3$ m/e 399.1958, found 399.1986.

EXAMPLE 35

The compounds of Examples 14–17, 22, 24, 25, 31 and 34 were tested for antibacterial activity and were found to be active against *Staphylococcus aureus*, *Staphylococcus epidermus*, *Streptoccocus pyogenes*, *E. coli*, Klebsiella, Pasteurella, Serratia, and *Neisseria gonorrhea* at levels lower than 15 micrograms per ml.

I claim:

1. A compound of formula

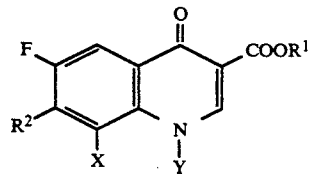

wherein $R^1$ is hydrogen, $C_1$-$C_6$ alkyl, or a pharmaceutically acceptable cation;

Y is cyclopropyl, ethyl or p-fluorophenyl, and X is hydrogen or fluoro, or X and Y taken together form a group

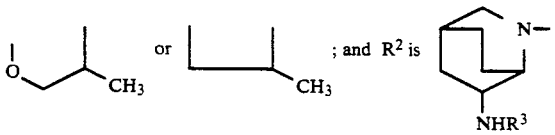

wherein $R^3$ is hydrogen or $C_1$-$C_4$ alkyl; or a pharmaceutically acceptable salt thereof.

2. A compound according to claim 1 wherein $R^2$ is

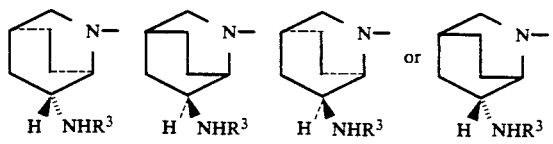

3. A compound according to claim 1 wherein $R^2$ is

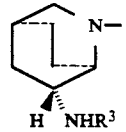

4. A compound according to claim 1 wherein $R^3$ is hydrogen.

5. A compound according to claim 3 wherein $R^3$ is hydrogen.

6. A compound according to claim 1 wherein Y is cyclopropyl.

7. A compound according to claim 3 wherein Y is cyclopropyl.

8. A compound according to claim 4 wherein Y is cyclopropyl.

9. A compound according to claim 5 wherein Y is cyclopropyl.

10. A compound according to claim 6 wherein Y is cyclopropyl.

11. A compound according to claim 1 wherein X is hydrogen.

12. A compound according to claim 3 wherein X is hydrogen.

13. A compound according to claim 4 wherein X is hydrogen.

14. A compound according to claim 5 wherein X is hydrogen.

15. A compound according to claim 6 wherein X is hydrogen.

16. A compound according to claim 7 wherein X is hydrogen.

17. A compound according to claim 8 wherein X is hydrogen.

18. A compound according to claim 9 wherein X is hydrogen.

19. A compound according to claim 10 wherein X is hydrogen.

20. An antibacterial pharmaceutical composition comprising an antibacterial effective amount of a compound according to claim 1 and a pharmaceutically acceptable carrier.

21. A method of treating bacterial infections in mammals comprising administering to a mammal in need of such treatment on antibacterial effective amount of a compound of claim 1.

* * * * *